(12) United States Patent
Wang et al.

(10) Patent No.: US 10,835,552 B2
(45) Date of Patent: Nov. 17, 2020

(54) METHOD FOR PREPARING LINSEED POLYSACCHARIDE HAVING ANTIVIRAL ACTIVITY AND IMMUNOLOGICAL ACTIVITY, AND USE OF THE LINSEED POLYSACCHARIDE

(71) Applicant: Jinan University, Guangzhou (CN)

(72) Inventors: Yong Wang, Guangzhou (CN); Martin J. T. Reaney, Saskatoon (CA); Xiaofeng Li, Guangzhou (CN); Wenzhen Liao, Guangzhou (CN); Shan Liang, Guangzhou (CN); Yinglai Teng, Guangzhou (CN); Youn Young Shim, Saskatoon (CA); Peta-Gaye Gillian Burnett, Saskatoon (CA)

(73) Assignee: Jinan University (CN)

( * ) Notice: Subject to any disclaimer, the term of this patent is extended or adjusted under 35 U.S.C. 154(b) by 106 days.

(21) Appl. No.: 15/741,530

(22) PCT Filed: Jun. 30, 2016

(86) PCT No.: PCT/CN2016/088048
§ 371 (c)(1),
(2) Date: Jan. 3, 2018

(87) PCT Pub. No.: WO2017/005134
PCT Pub. Date: Jan. 12, 2017

(65) Prior Publication Data
US 2018/0193373 A1    Jul. 12, 2018

(30) Foreign Application Priority Data

Jul. 3, 2015    (CN) .......................... 2015 1 0391862

(51) Int. Cl.
| *A61K 31/715* | (2006.01) |
| *C08B 37/00* | (2006.01) |
| *A23L 33/125* | (2016.01) |
| *A61P 37/04* | (2006.01) |
| *A61P 31/20* | (2006.01) |
| *A61K 36/55* | (2006.01) |

(52) U.S. Cl.
CPC .......... *A61K 31/715* (2013.01); *A23L 33/125* (2016.08); *A61K 36/55* (2013.01); *A61P 31/20* (2018.01); *A61P 37/04* (2018.01); *C08B 37/0003* (2013.01); *A23V 2002/00* (2013.01); *A61K 2236/00* (2013.01); *Y02A 50/30* (2018.01)

(58) Field of Classification Search
None
See application file for complete search history.

(56) References Cited

U.S. PATENT DOCUMENTS 6,767,565 B2 *    7/2004    Shukla .................. A61K 36/00
424/725

FOREIGN PATENT DOCUMENTS

| CN | 1221771 A | 7/1999 |
| CN | 1242952 A | 2/2000 |
| CN | 1263139 A | 8/2000 |
| CN | 1613876 A | 5/2005 |
| CN | 101502532 A | 8/2009 |
| CN | 101503477 A | 8/2009 |
| CN | 105037573 A | 11/2015 |
| JP | 200491780 A | 3/2004 |

OTHER PUBLICATIONS

Quian et al. (Food Hydrocolloids, 2012 p. 275-283).*
Tan et al. (Engeenering, 2011, p. 1090-1094).*
Mao, "Extraction, Separation, Purification and Structure of Flaxseed Shell Polysaccharides", Zhejiang Gongshang University, 2012, 18 pages, English-language Abstract.
Xiao-Feng et al., "Research Progress of Flaxseed Gum", Guangzhou, China, 2014, pp. 55-59, English-language Abstract.

* cited by examiner

*Primary Examiner* — Agnieszka Boesen
(74) *Attorney, Agent, or Firm* — The Webb Law Firm

(57) ABSTRACT

Disclosed are a method for preparing a linseed polysaccharide having antiviral activity and immunological activity, food and healthare products and methods of treatment using the linseed polysaccharide. The method comprises the steps of: using the linseeds as raw materials, pulverizing the linseeds, separating the husks from the kernels of the linseeds, extracting by the microwave-assisted hot water extraction, deproteinizing by the Sevage method, carrying out ethanol precipitation, and freeze-drying to obtain the linseed crude polysaccharides, then carrying out ion-exchange column chromatography, Sephadex gel column chromatography, and ultra-filtration so as to obtain the linseed triple-helix polysaccharides.

5 Claims, 9 Drawing Sheets

METHOD FOR PREPARING LINSEED POLYSACCHARIDE HAVING ANTIVIRAL ACTIVITY AND IMMUNOLOGICAL ACTIVITY, AND USE OF THE LINSEED POLYSACCHARIDE

CROSS-REFERENCE TO RELATED APPLICATIONS

This application is the United States national phase of International Application No. PCT/CN2016/088048 filed Jun. 30, 2016, and claims priority to Chinese Patent Application No. 201510391862.6 filed Jul. 3, 2015, the disclosures of each of which are hereby incorporated by reference in their entireties.

BACKGROUND OF THE INVENTION

Technical Field

The invention belongs to the fields of biological medicines and functional foods, in particular to a method for preparing a linseed polysaccharide having antiviral activity and immunological activity, and use of the linseed polysaccharide.

Background Art

Flax (*Linum ustitatissimum L.*), also referred to as fiber-flax, is a member of *Linaceae, Linum Linn*. As a traditional oil crop, linseed is rich in a variety of nutritional ingredients, such as unsaturated fatty acids, essential amino acids, vitamin E, carbohydrates and the like, wherein the polysaccharide substances are mainly present in the linseed husks, and the contents thereof vary with the production areas and the varieties.

Polysaccharide, also refers to as polysaccharid, is a macromolecular compound which is formed by connecting more than 10 monosaccharides via glycosidic bonds, having a relative molecular weight from tens of thousands to millions. Polysaccharides are widespread in nature, and are present in high plants, algae, fungi and animal bodies. For example, fungal polysaccharides, plant polysaccharides, animal polysaccharides, algal polysaccharides, bacterial polysaccharide and the like, are the most abundant biological polymers in nature, and about 300 kinds of natural polysaccharide compounds are well-known. Polysaccharides have various biological functions, such as cell specific recognition, receptors on cell surfaces for various antigens and drugs, activation of immune cells and the like. Particularly, as plant polysaccharides have various biological activities, such as immunoregulation, anti-tumor, anti-aging, reduction of blood sugar and the like, they attract increasing interests in the world. The plant polysaccharides, as natural active substances, have the greatest advantages of low toxic and side effects and widespread sources. In addition, the research shows that the polysaccharides having the triple-helix structure are significantly higher than other polysaccharides in the immunoregulation function, and generally have higher antiviral activity. The polysaccharide substances have a wide variety of physiological functions, and almost have no toxic or side effects on the bodies, therefore they are the ideal pharmaceutical excipients.

The traditional methods for exacting the linseed polysaccharides are mainly the hot water extraction method, the patents related to the extraction of the linseed polysaccharide in the prior art comprise Chinese Patent Application Publication Nos: CN1221771, CN1242952 and CN1263139, these patents are all involved in the improvements on the traditional processes for hot water extraction of linseed gum, and the extracted linseed polysaccharides have no triple-helix high-level structure and antiviral activity.

SUMMARY OF THE INVENTION

In some examples, there is provided a method for preparing a linseed polysaccharide having antiviral activity and immunological activity, comprising: (1) separation of the husks from the kernels of the linseeds: pulverizing the linseeds, sieving the pulverized linseeds to form linseed powder, then thoroughly mixing the linseed powder(s) with a combined solvent, centrifuging for 20-30 minutes, and respectively collecting the linseed kernels in the upper layer and depositing the linseed husks in the bottom layer; (2) extraction of the linseed polysaccharides: extracting polysaccharides from the linseed husks obtained in step (1) by microwave-assisted hot water extraction, sieving the extracted solutions, collecting the concentrated solutions, and freeze-drying the concentrated solutions under vacuum; (3) separation of the linseed polysaccharides: deproteinizing the freeze-dried crude extracts obtained in step (2) 25-30 times by the Sevage method, centrifuging at a speed of 3500-5000 r/min for 20-30 min, separating the supernatants; adding anhydrous ethanol into the supernatants, standing for precipitation for 4-12 h, centrifuging at a speed of 3500-5000 r/min for 20-30 min, taking the precipitates, and freeze-drying the precipitates under vacuum, so as to obtain the linseed husk crude polysaccharides; (4) purification of the linseed polysaccharides: formulating the linseed husk crude polysaccharides obtained in step (3) into 5-8 mg/mL solutions, purifying by a chromatographic column A, eluting with water, and detecting the polysaccharides by a phenol-sulfuric acid method, combining the collection liquids showing a positive result in the sugar reaction, concentrating by rotary evaporation at 50-60° C., dialyzing, then freeze-drying under vacuum; formulating the dried polysaccharides into 2-5 mg/mL solutions, purifying by a chromatographic column B, eluting with distilled water, collecting the polysaccharide components, dialyzing, ultra-filtrating, concentrating and freeze-drying, so as to obtain the linseed polysaccharide having antiviral activity and immunological activity, food healthcare products comprising the linseed polysaccharide, and methods of preventing and/or treating hepatitis B virus (HBV) infection, treating immune deficiency or improving immunity in a subject, comprising administering to a subject the linseed polysaccharide in an effective amount.

Also disclosed is a method for preparing a linseed polysaccharide having antiviral activity and immunological activity and use of the linseed polysaccharide. The method comprises the steps of: using the linseeds as raw materials, pulverizing the linseeds, separating the husks from the kernels of the linseeds, extracting by the microwave-assisted hot water extraction, deproteinizing by the Sevage method, carrying out ethanol precipitation, and freeze-drying to obtain the linseed crude polysaccharides, then carrying out ion-exchange column chromatography, Sephadex gel column chromatography, and ultra-filtration so as to obtain the linseed triple-helix polysaccharides. The FHP-1 of the present invention has uniform components and has a molecular weight of 2626 kDa. The invention, for the first time, discloses a polysaccharide having a triple-helix structure separated from the linseeds. It is proved through cytobiological experiments that the polysaccharide can reduce the expressions of hepatitis B surface antigen and hepatitis B e-antigen, inhibit the replication of hepatitis B virus DNA, activate immune responses, and increase the secretions of tumor necrosis factor TNF-α, interleukins IL-6 and IL-12, and inflammatory factor NO from immune cells. Finally, the prepared linseed triple-helix polysaccharides are applied to the functional foods, such as anti-virus food drinks or yoghurts, thus achieving the applications in the functional foods for prevention of hepatitis B virus HBV infection, treatment of immune defect or improvement of immunity, and the like.

TECHNICAL PROBLEM

In order to solve the defects and deficiencies in the prior art, the primary object of the present invention is to provide a method for preparing a linseed polysaccharide having antiviral activity and immunological activity.

Another object of the present invention is to provide a linseed polysaccharide having antiviral activity and immunological activity obtained by the abovementioned method.

A further object of the present invention is to provide use of the abovementioned linseed polysaccharide having antiviral activity and immunological activity.

Technical solution

In order to achieve the above objects of the present invention, the technical solutions of the present invention are as follows:

A method for preparing a linseed polysaccharide having antiviral activity and immunological activity, comprises steps of:

(1) Separation of the husks from the kernels of the linseeds: Chinese linseed (from Zhangjiakou City, HeBei Province, China), Canadian linseed (CDC-glass, CDC-Bethune, Camelina) and the Canadian Radish seeds are respectively subjected to ambient temperature pretreatment and frozen pretreatment, then pulverized with a disc mill and a rolling mill, and sieved, the sieved linseed powders are thoroughly mixed with combined solvents (glycerol and ethanol; glycerol and water; glycerol triacetate and ethanol; glycerol triacetate and water; PEG 300-800 and ethanol; and PEG 300-600 and water) in different proportions, centrifuged for 5~30 min, and respectively collected the linseed kernels in the upper layer and the linseed husks deposited in the bottom layer, removed the solvent residues by using ethanol and isopropanol, then dried in the air, so as to obtain the dried linseed kernels and linseed husks.

(2) Extraction of the linseed polysaccharides: the linseed husks obtained in step (1) are used as raw materials, extracted the polysaccharides by the microwave-assisted hot water extraction, sieved the extracted solutions, collected the concentrated solutions, and freeze-dried in vacuum.

(3) Separation of the linseed polysaccharides: the freeze-dried crude extracts obtained in step (2) are deproteinized 25~30 times by Sevage method, centrifuged at a speed of 3500~5000 r/min for 20~30 min, and taken the supernatants; added anhydrous ethanol into the supernatants, stood for precipitation (i.e., alcohol precipitation) for 4~12 h, centrifuged at a speed of 3500~5000 r/min for 20~30 min, taken the precipitates, and freeze-dried in vacuum, so as to obtain the linseed crude polysaccharides.

(4) Purification of the linseed polysaccharides: the linseed husk crude polysaccharides obtained in step (3) are formulated into 5~8 mg/mL solutions, purified by a chromatographic column A, eluted with water, and detected the polysaccharides by the phenol-sulfuric acid method, combined the collection liquids showing the positive result in the sugar reaction, concentrated by rotary evaporation at 50~60° C., dialyzed, then freeze-dried in vacuum; the dried polysaccharides are formulated into 2~5 mg/mL solutions, purified by a chromatographic column B, eluted with distilled water, collected the polysaccharide components, dialyzed, ultra-filtrated, concentrated and freeze-dried, so as to obtain the linseed polysaccharides having antiviral activity and immunological activity (FHP~1).

(5) Application of the linseed polysaccharides: the linseed polysaccharides obtained in step (4) are added into the commercially available fruit juices in a proportion of 1~5%, thus achieving the application of the prepared linseed polysaccharides in the food products.

The separation of the husks from the kernels of the linseeds in step (1), is carried out as follows: according to the combined solvents in different volume ratios, which comprise glycerol (65%~100%) and ethanol (35%~0%); glycerol (60%~100%)) and water (40%~100%); glycerol triacetate (90%~100%) and ethanol (10%~0%); glycerol triacetate (75%~100%) and water (25%~100%), PEG 300 (90%~100%) and ethanol (10%~0%); PEG 300 (85%~0%) and water (15%~100%); the husks and the kernels of the linseed are effectively separated by virtue of the density differences.

The microwave-assisted hot water extraction in step (2) is carried out under the conditions as follows: the solid-to-liquid ratio is 1:20~1:30 (w/v), and the extraction temperature is 60~100° C., the extraction time is 40~60 min, and the output power is 600~800 W, the stirring speed is 600~900 r/min, and the extracted solution obtained by the microwave-assisted hot water extraction is sieved via a 100 mesh sieve.

The method for formulating the Sevage reagent in step (3) comprises that chloroform and n-butanol are mixed in a volume ratio of 3:1~5:1.

The method of deproteinization by Sevage method in step (3) comprises that the freeze-dried crude extract in step (2) is mixed with the Sevage reagent in a volume ratio of 1:1~1:3, shaken for 20~30 min, centrifuged at a speed of 3500~5000 r/min for 20~30 min, and taken the upper polysaccharide solution; repeated the abovementioned steps 25~30 times (i.e., the obtained upper solution is repeatedly subjected to the following treatment processes 25~30 times: mixing with the Sevage reagent in a volume ratio of 1:1~1:3, shaking for 20~30 min, centrifuging at a speed of 3500~5000 r/min for 20~30 min, and taking the upper solution).

The amount of anhydrous ethanol in step (3) is 3~5 times of the volume of the linseed husk crude polysaccharide solution (which refers to the upper solution), and after adding anhydrous ethanol, the solution is stood for precipitation at 4° C. for 4~12 h.

The chromatographic column A in the process for purification of the linseed polysaccharides in step (4) is DEAE-Sepharose Fast Flow ion exchange column, and the chromatographic column B is Sephadex G-100 Sephadex gel column, the membrane in the ultra-filtration process has a molecular weight cutoff of $1 \times 10^6$ Da; the dialysis time is 48 h, and the dialysis bag has a molecular weight cutoff of 3000~5000 Da.

The linseed polysaccharide having antiviral activity and immunological activity obtained by the abovementioned preparation method (FHP-1) is a linseed triple-helix polysaccharide (FHP-1), which has uniform components, has an average molecular weight of 2626 kDa as measured by gel permeation chromatography (GPC), and are mainly composed of seven monosaccharides, i.e., rhamnose, arabinose, xylose, galactose, mannose, glucose and fucose, as determined by the gas chromatography after derivatization.

The linseed polysaccharide having antiviral activity and immunological activity has a special structure comprising triple-helix structures and triple-helix groups, and simultaneously has the functions of resisting hepatitis B virus and enhancing immune response.

As the linseed polysaccharide having antiviral activity and immunological activity (FHP-1) has the functions of both resisting hepatitis B virus and enhancing immune response, it can be used in a functional food for preventing hepatitis B virus (HBV) infection, treating immune defects or improving immunity.

Beneficial Effects

As compared with the prior art, the present invention has the advantages and the beneficial effects as follows:

(1) In the present invention, a microwave-assisted extraction technology is introduced in the traditional hot water extraction method, and by virtue of the heat effect of microwave, the solvents in the extraction system can more efficiently destroy the cell walls in the skin tissues of the linseed husks, so that the polysaccharide contents can be more efficiently extracted. As compared with the traditional hot water extraction method (under the conditions that the temperature and the solid-to-liquid ratio are the same), in the case that the linseed triple-helix polysaccharides are obtained with the same extraction rate, the method in the present invention reduces the extraction times by 6-8 times, which greatly improves the extraction efficiency.

(2) In order to deeply exploit and utilize the linseed resources, the chemical structure identification, antiviral test and immunoregulation activity test are carried out on the separated and purified linseed triple-helix polysaccharides. The present invention, for the first time, provides the effective separation of the husks from the kernels of the linseeds by utilizing glycerol and ethanol in different proportions, and for the first time, shows in the structure identification that the linseed triple-helix polysaccharide has triple-helix high-level structure and triple-helix group, and for the first time, proves that the linseed triple-helix polysaccharide has anti-hepatitis B virus activity and immunoregulation activity, and has broad application prospects in the fields of medicaments for preventing HBV and the foods and healthcare products for improving the body's immune functions.

As shown in the Congo red experimental analysis, the maximum absorption wavelength of the complex formed by the linseed triple-helix polysaccharide (FHP-1) and Congo red occurs red shift, as compared with that of the blank control, Congo red. This result shows that FHP-1 and Congo red can form a complex, which has a regular triple-helix conformation. The element analysis shows that it contains 0.85% of S element, the content of the sulfuric acid group in the FHP-1 is 2.63% as measured by the Barium sulfate turbidimetric method, and in combination with the infrared spectrum, 1244 cm$^{-1}$ represents S=O stretching vibration, and 823.71 cm$^{-1}$ represents that the sulfuric acid group lies in the equatorial position of the monosaccharide residue, so that it shows that a small amount of triple-helix structures are present in the linseed triple-helix polysaccharide FHP-1.

The toxicity tests show that the linseed triple-helix polysaccharides (FHP-1) of the present invention have no cytotoxicity on the HepG2.2.15 and RAW264.7 cells, under the concentration of 1000 mg/mL; as compared with the blank control group, the FHP-1 drug groups can significantly reduce the expressions of hepatitis B surface antigen (HBsAg) and hepatitis B e-antigen (HBeAg), and inhibit the expression level of the hepatitis B virus DNA, and at the same time FHP-1 significantly increases the secretion of tumor necrosis factor TNF-α, interleukin IL-6 and IL-12, and inflammatory factor NO from the mouse macrophage RAW 264.7 cells, has significant antiviral activity and immunoregulation function, so that it can be used in the medicament for preventing HBV and a food and a healthcare product for improving the body's immune function. The method for preparing the linseed triple-helix polysaccharide of the present invention is simple and reliable, therefore it can be implemented on a large scale.

(3) In the present invention, the linseed raw material sources are widespread and the preparation method is simple and reliable, the product has high safety and no toxic and side effects, and can be produced on a large scale, so that it is expected to be developed into medicaments for preventing hepatitis B and functional foods for improving body's immunity.

DETAILED DESCRIPTION OF THE INVENTION

EXAMPLES

Figure 1:
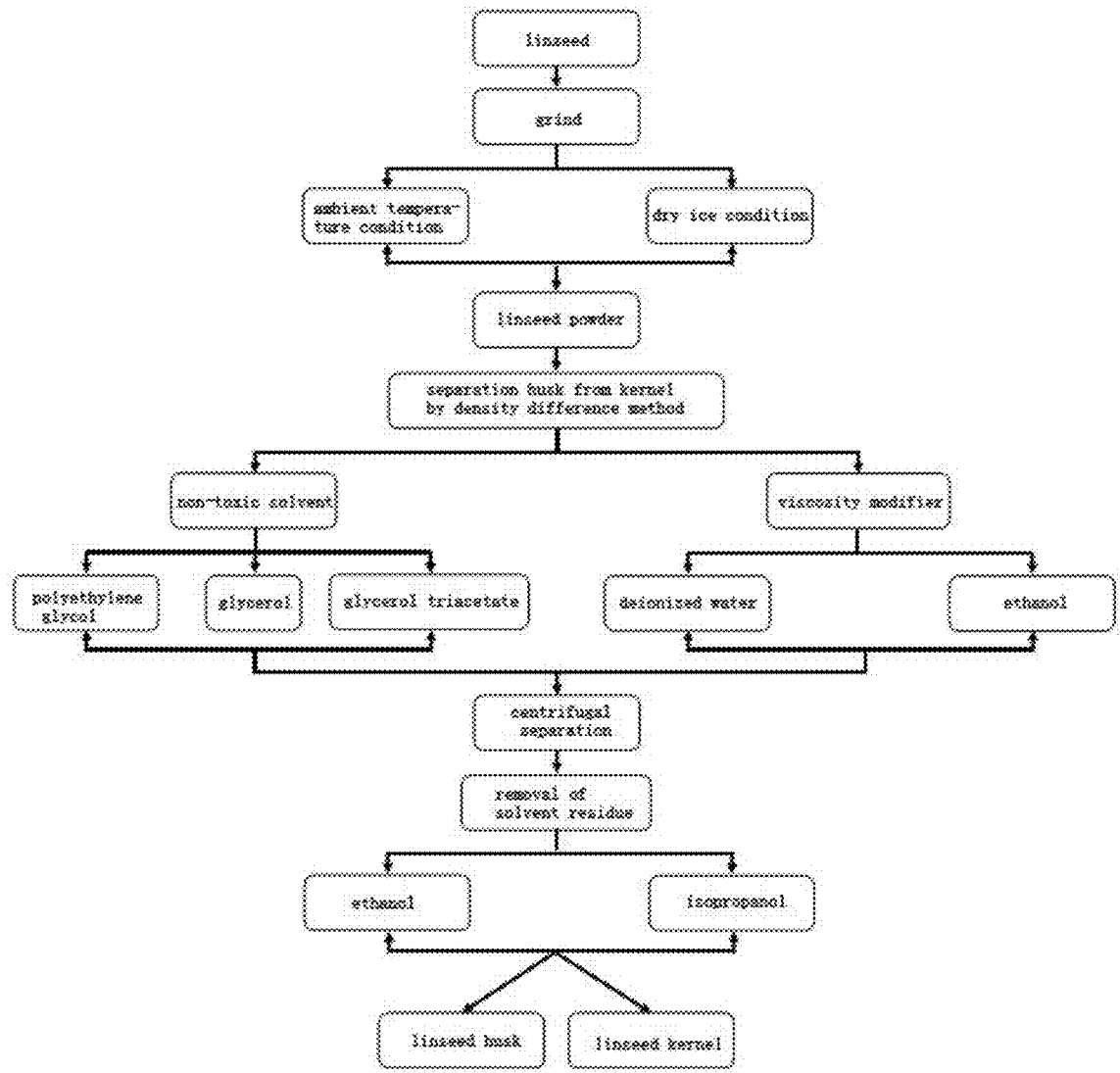
FIG. 1 shows a process flow chart for separating the husks from the linseeds.

The present invention is further described in detail below in combination with the examples and drawings, but embodiments of the present invention are not limited thereto.

Example 1. Preparation of the Linseed Triple-Helix Polysaccharide

The preparation of the linseed triple-helix polysaccharide comprised the steps of:

Separation of the husks from the kernels of the linseeds: the linseeds were subjected to ambient temperature pretreatment, pulverized by a disc mill, sieved, then mixed thoroughly the sieved linseed powders with combined solvents (100% glycerol; 100% glycerol triacetate; 100% PEG 300), centrifuged for 20 min, collected the linseed kernels in the upper layer and the linseed husks deposited in the bottom layer respectively, removed the solvent residues by using ethanol and dried in the air, finally collected the dried linseed husks and the linseed kernels.

(2) Extraction of the linseed polysaccharides: 250 g the linseed husks obtained in step (1) were taken as raw materials, exacted the linseed polysaccharides by microwave-assisted hot water extraction under the condition that the solid-to-liquid ratio was 1:20 (g/mL), the extraction temperature was 60° C., the extraction time was 40 min, the output power was 600 W and the stirring speed was 600 r/min, sieved the extracted solution via a 100 mesh sieve, collected the concentrated solution, and freeze-dried under vacuum.

(3) Separation of the linseed polysaccharides: the freeze-dried crude extracts obtained in step (2) were deproteinized 25 times by the Sevage method, centrifuged at a speed of 3500 r/min for 20 min, and taken the supernatants; added 3 volumes of anhydrous ethanol into the supernatants, carried out alcohol precipitation at 4° C. for 4 h, centrifuged at a speed of 3500 r/min for 20 min, taken the precipitates, and freeze-dried under vacuum, so as to obtain about 8.35 g of the linseed husk crude polysaccharides.

Figure 3:
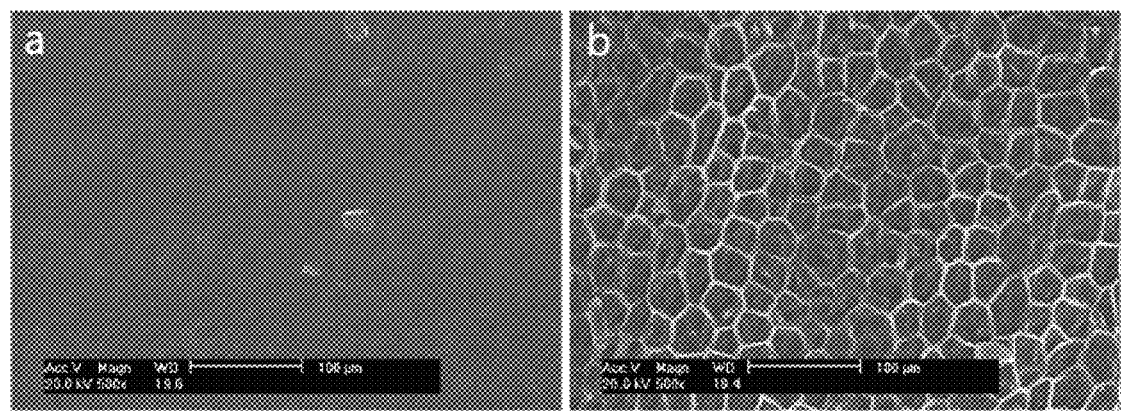
FIG. 3 shows the scanning electron microscopy images of the surface of the linseed husk, wherein a: pre-microwave-assisted extraction, and b: post-microwave-assisted extraction.

(4) Purification of the linseed polysaccharides: the linseed husk crude polysaccharides obtained in step (3) were formulated into 5 mg/mL solutions, loaded on DEAE-Sepharose Fast Flow column (the elution curve was shown in FIG. 3), carried out stepwise elution sequentially with 0~2.0 mol/L NaCl solution, collected in the collection tubes, detected the polysaccharides by the phenol-sulfuric acid method, combined the collection liquids showing the positive result in the sugar reaction, concentrated by rotary evaporation at 50° C., dialyzed for 48 h (3000~5000 Da), then freeze-dried under vacuum; formulated the dried polysaccharides into 2 mg/mL solutions, loaded on Sephadex G-100 Sephadex gel column, eluted with distilled water, collected the polysaccharide components, dialyzed again, ultra-filtrated by a membrane having a molecular weight cutoff of $1\times10^6$ Da, collected the retentates separately, concentrated, and freeze-dried, so as to obtain the linseed triple-helix polysaccharide (FHP-1) sample having a molecular weight of more than $1\times10^6$ Da.

Example 2. Preparation of the Linseed Triple-Helix Polysaccharides

Preparation of the linseed triple-helix polysaccharides comprised the steps of:

Separation of the husks from the kernels of the linseeds: the linseeds were subjected to ambient temperature pretreatment, pulverized by a rolling mill, sieved, mixed thoroughly the sieved linseed powders with combined solvents (65% glycerol and 35% ethanol; 40% glycerol and 60% water; 90% glycerol triacetate and 10% ethanol; 75% glycerol triacetate and 25% water; 90% PEG 300 and 10% ethanol; 85% PEG 300 and 15% water), centrifuged for 30 min, collected the linseed kernels in the upper layer and the linseed husks deposited in the bottom layer respectively, removed the solvent residues by using isopropanol, and dried in the air, finally collected the dried linseed husks and the linseed kernels.

(2) Extraction of linseed polysaccharides: 250 g the linseed husks obtained in step (1) were taken as raw materials, exacted the linseed polysaccharides by microwave-assisted hot water extraction under the conditions that the solid-to-liquid ratio was 1:30 (g/mL), the extraction temperature was 100° C., the extraction time was 60 min, the output power was 800 W, and the stirring speed was 900 r/min, sieved the extracted solution via a 100 mesh sieve, collected the concentrated solution, and freeze-dried under vacuum.

(3) Separation of the linseed polysaccharides: the freeze-dried crude extracts obtained in step (2) were deproteinized 30 times by the Sevage method, centrifuged at a speed of 5000 r/min for 30 min, and taken the supernatants; added 5 volumes of anhydrous ethanol into the supernatants, carried out alcohol precipitation at 4° C. for 12 h, centrifuged at a speed of 5000 r/min for 30 min, taken the precipitates, and freeze-dried under vacuum, so as to obtain about 11.55 g of the linseed husk crude polysaccharides.

(4) Purification of the linseed polysaccharides: the linseed husk crude polysaccharides obtained in step (3) were formulated into 10 mg/mL solutions, loaded on DEAE-Sepharose Fast Flow column (the elution curve was shown in FIG. 3), carried out a stepwise elution with 0~2.0 mol/L NaCl solution sequentially, collected in the collection tubes, detected the polysaccharides by the phenol-sulfuric acid method, combined the collection liquids showing the positive result in the sugar reaction, concentrated by rotary evaporation at 60° C., dialyzed for 48 h (3000~5000 Da), then freeze-dried under vacuum; formulated the dried polysaccharides into 5 mg/mL solutions, loaded on Sephadex G-100 Sephadex gel column, eluted with distilled water, collected the polysaccharide components, dialyzed again, ultra-filtrated by a membrane having a molecular weight cutoff of $1\times10^6$ Da, collected the retentates separately, concentrated, and freeze-dried, so as to obtain the linseed triple-helix polysaccharide sample having a molecular weight of more than $1\times10^6$ Da (FHP-1).

Example 3. Purity Identification of the Linseed Triple-Helix Polysaccharides (FHP-1)

Figure 4:
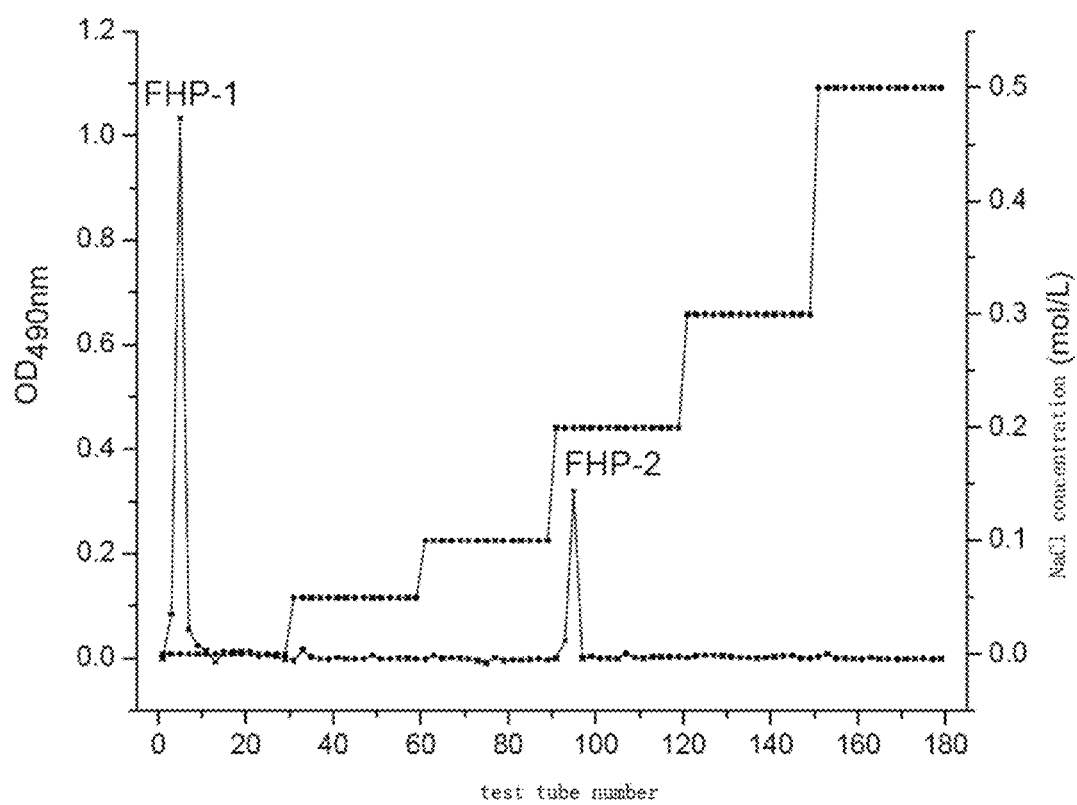
FIG. 4 shows the DEAE-Sepharose Fast Flow elution curve for purifying the linseed crude polysaccharide.

The purity determinations were carried out on the separated and purified linseed triple-helix polysaccharides (FHP-1) in example 2 by GPC. The test conditions and methods were as follows: TSK G-5000PWXL and TSK G-3000PWXL chromatographic columns were connected to the 2414-type Differential Refraction Index Detector in series, the column temperature was 35° C., the mobile phase was 0.02 mol/L $KH_2PO_4$, and the flow rate was 0.6 mL/min. 2.0~2.5 mg of the sample was accurately weighed, dissolved in 1 mL mobile phase, passed through 0.22 µm filter membrane, loaded 10 µL sample manually. The GPC chromatogram was shown in FIG. 4. The purities of the polysaccharide components were determined on the basis of the chromatograms, and the result showed that the purified FHP-1 was a polysaccharide having uniform molecular weight of about 2626 kD.

Example 4. Determination of the Monosaccharide Composition of the Linseed Triple-Helix Polysaccharides (FHP-1)

Figure 5:
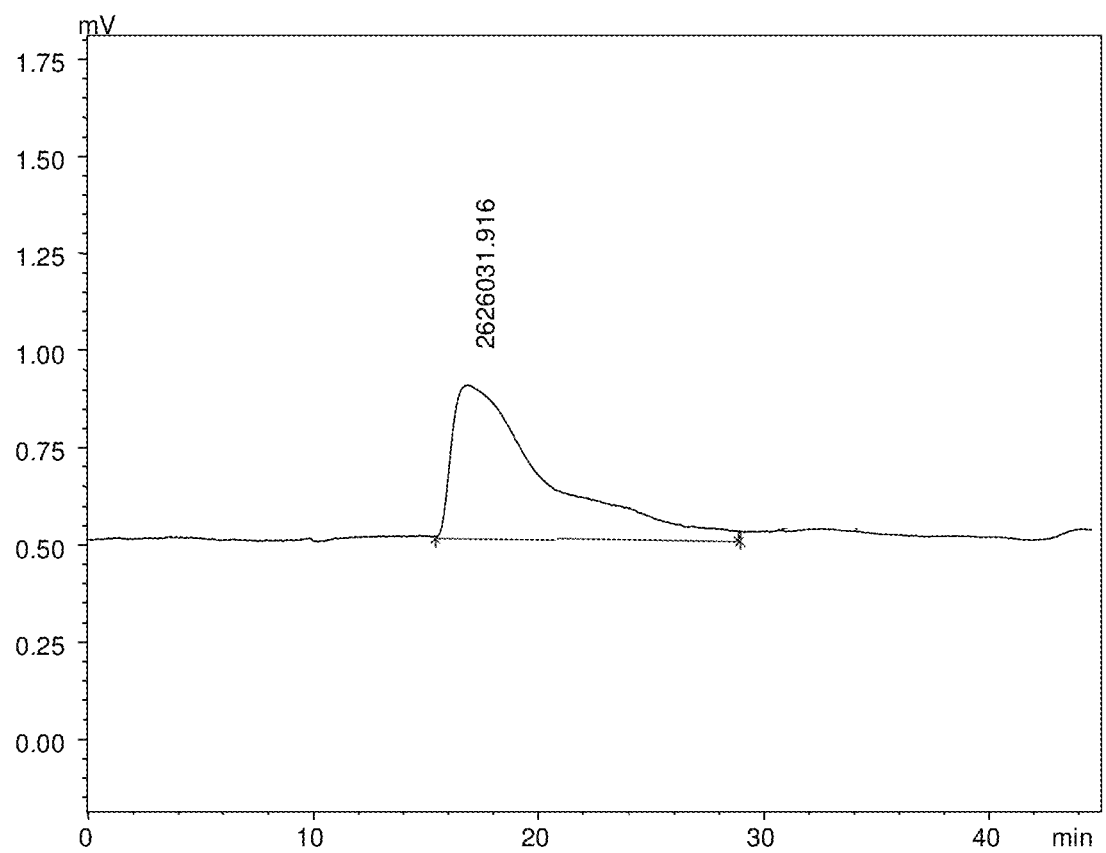
FIG. 5 shows a GPC chromatogram of the linseed triple-helix polysaccharide (FHP-1).

10 mg the linseed triple-helix polysaccharide sample prepared in example 2 was taken, added 4.0 mL of 2 mol/L trifluoroacetic acid, hydrolyzed at 100~120° C. for 6~8 h to obtain the monosaccharides, then added 0.5 mL pyridine, reacted at 90° C. for 0.5 h, cooled then added 0.5 mL acetic anhydride, and reacted at 90° C. for 0.5 h, cooled then added water and chloroform to extract three times, taken the chloroform layer and evaporated to dryness, dissolved the residues with chloroform, filtered through 0.22 μm vacuum filter, analyzed by GC. The gas chromatography conditions were as follows: HP-5 quartz capillary column (30 m×0.32 mm×0.25 μm) was used; the carrier gas was $N_2$; the injection volume was 1 μL; the flow rate was 1 mL/min; in splitless injection mode, the injection port temperature was 250° C.; the temperature of the FID detector was set to 250° C.; carried out a programmed-temperature procedure: the initial temperature was 100° C., the temperature was kept for 0.5 min; the temperature was increased to 160° C. at a heating rate of 3° C./min; then the heating rate was changed, and the heating was continued, the temperature was increased to 250° C. at a heating rate of 10° C./min, and the temperature was kept for 5 min. The determination results of the FHP-1 monosaccharide composition was shown in FIG. 5, in combination with the gas chromatograms of the monosaccharide standards, it showed that the FHP-1 was mainly composed of seven monosaccharides, i.e., rhamnose, arabinose, xylose, galactose, mannose, glucose and fucose.

Figure 2:
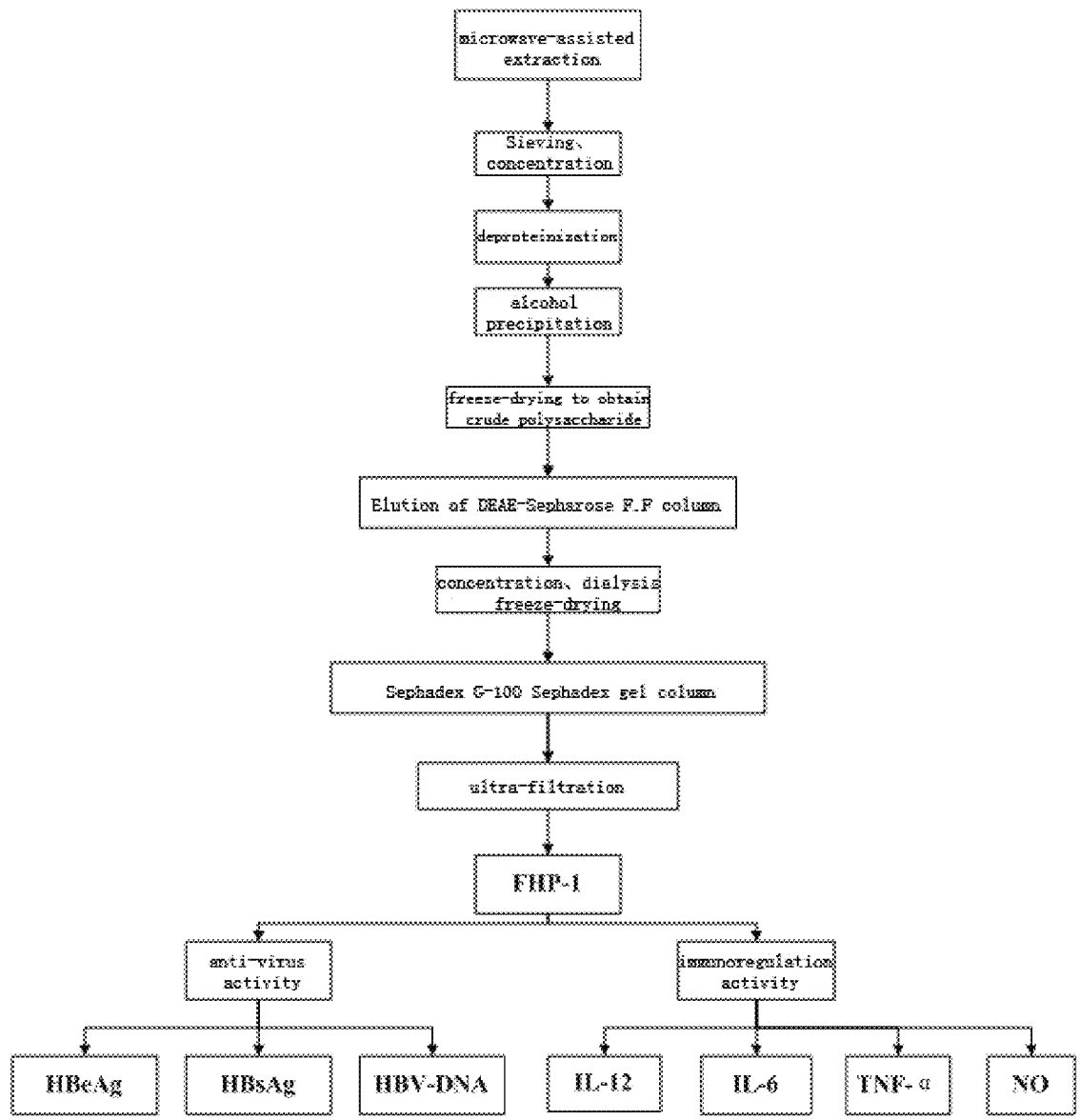
FIG. 2 shows a technical flow chart for extraction and purification and application of linseed triple-helix polysaccharide.

Example 5. The Scanning Electron Microscopy Images of the Linseed Husks and the Analysis of Congo Red Experiment 1~2 mg pre- or post-extracted linseed husks were randomly selected, and placed on a copper stage, compared the differences of the linseed husk surfaces between pre- and post-microwave-assisted extraction by scanning electron microscopy, as shown in FIG. 2, (a): pre-microwave-assisted extraction, (b): post-microwave-assisted extraction, the linseed husk surfaces changed from smooth colloid film to obvious uneven one, possibly due to the fact that the microwaves penetrated through the extraction medium to reach the interior of the materials, caused the internal pressure of the cells exceeding the maximum pressure which can be withstood by the cell walls, and caused the cells to break and release the internal active ingredients.

Figure 6:
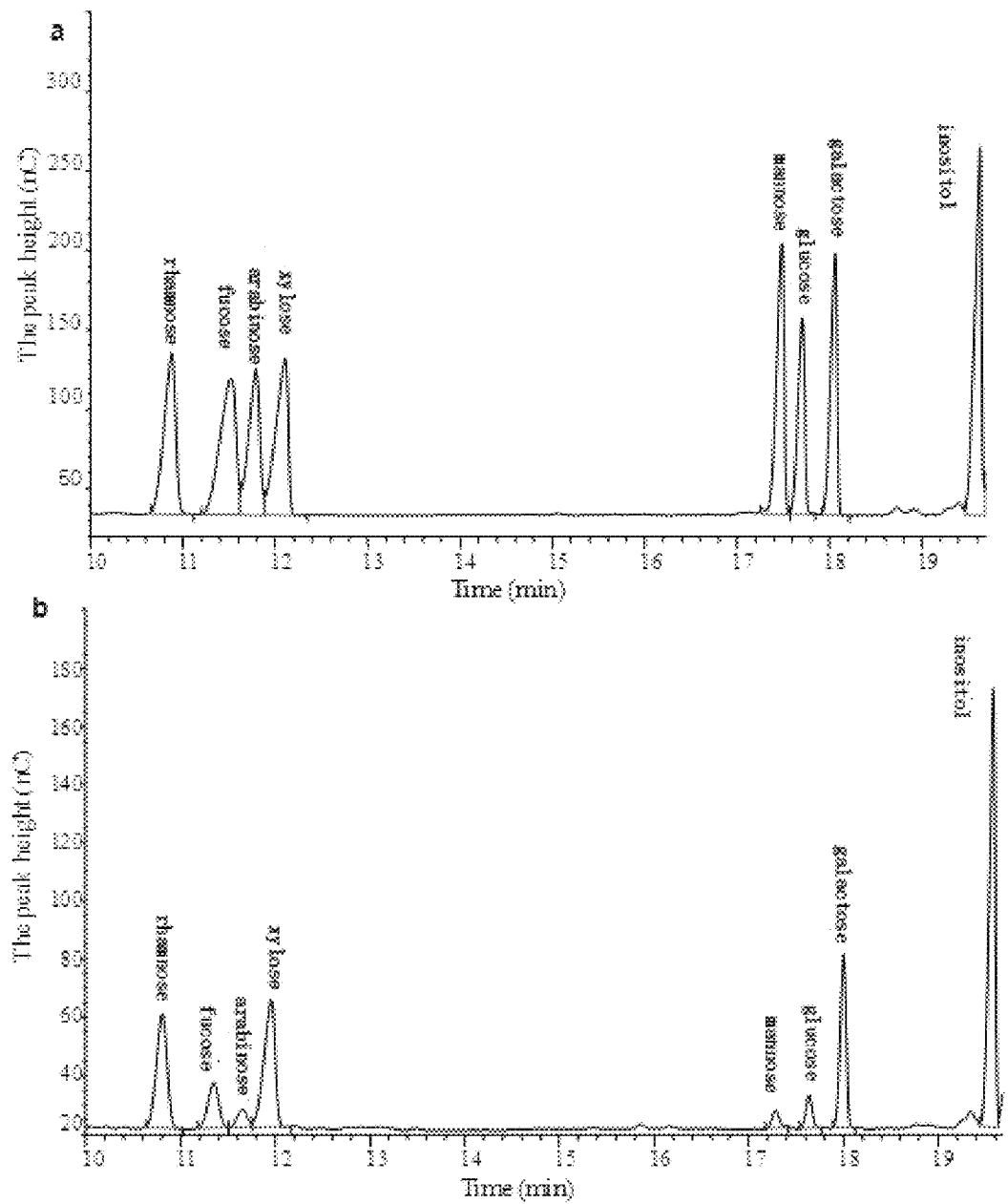
FIG. 6 shows a chromatogram for determining the monosaccharide composition of the linseed triple-helix polysaccharide (FHP-1), wherein a: gas chromatogram of the monosaccharide standards, b: gas chromatogram of FHP-1 after hydrolysis and derivatization.
Figure 7:
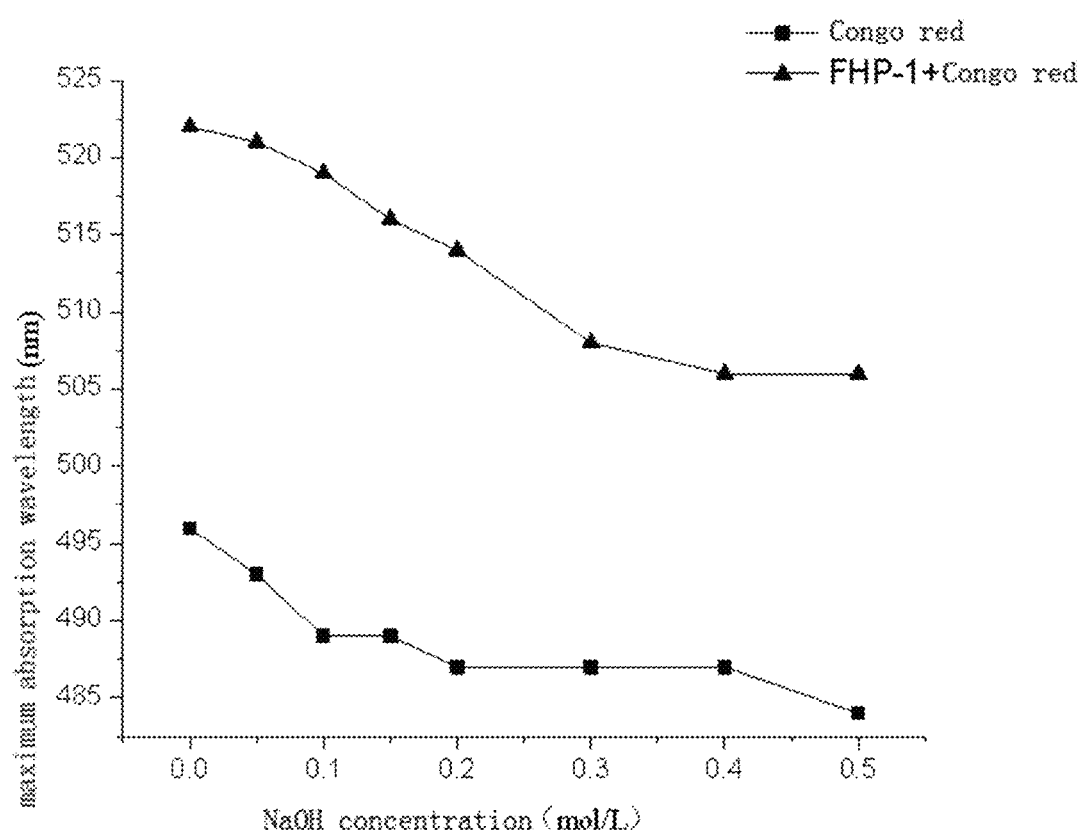
FIG. 7 shows an experiment spectrum of the linseed triple-helix polysaccharide (FHP-1) and Congo red.

An amount of FHP-1 polysaccharides prepared in example 2 were formulated into 2 mL of 1~2 mg/mL solutions, added 2 mL Congo red reagent (100 μmol/L), and added NaOH solution (1 mol/L) dropwise to increase the final concentration of the alkaline solution gradually from 0 mol/L to 0.5 mol/L. The full-wavelength scanning results were recorded, and compared to a blank control. The results were shown in FIG. 6. The maximum absorption wavelength of the complex formed from FHP-1 and Congo red occurred a red shift as compared to that of the blank control, Congo red. It was indicated that FHP-1 and Congo red can form a complex, which had a regular triple-helix conformation. Such ordered structure having a triple-helix conformation was thought as an important factor in contributing to the immunological activity.

Example 6. Anti-Virus Activity Assay of the Linseed Triple-Helix Polysaccharides (FHP-1)

MTT assay: The activated HepG2.2.15 cells in the logarithmic growth phase were seeded in 96-well plate at a concentration of $1\times10^6$ cells/mL, cultured at 37° C., under 5% $CO_2$ for 24 h. The groups which were added with 150 μL the linseed triple-helix polysaccharides, as the drug groups, were continued to culture for 24 h, with the group having no drugs as a blank control. 20 μL MTT solution was added, continued to culture for 4 h, then stopped to culture. The culture medium in the well was aspirated. 150 μL dimethyl sulfoxide was added into each well. The plates were shaken at a low speed in a shaker for 10 min until the crystals were fully dissolved.

The formula for calculating the cell survival rate was as follows:

Survival rate=$A_1/A_0$, wherein $A_1$ is the absorbance of the sample group in a parallel test, and $A_0$ is the absorbance of the control group in a parallel test.

Figure 8:
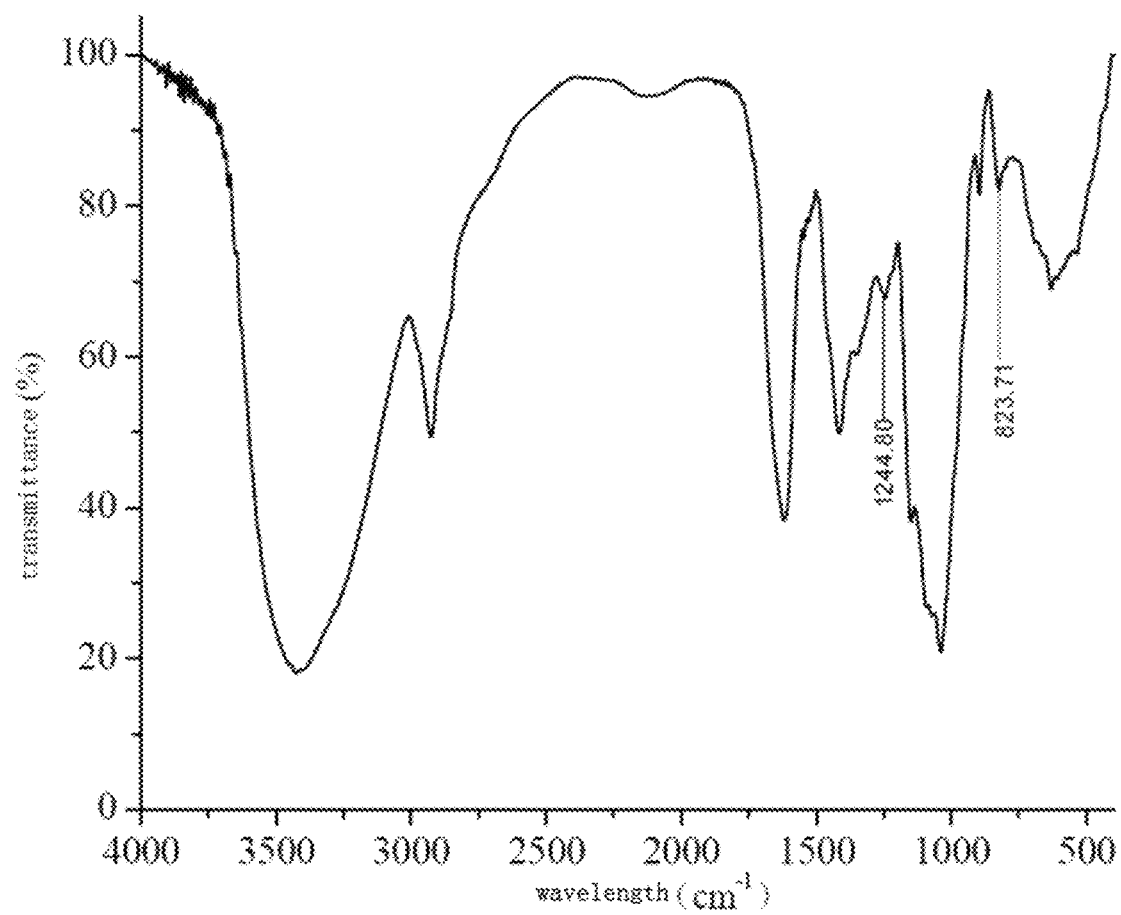
FIG. 8 shows an infrared spectrum of the linseed triple-helix polysaccharide (FHP-1).

The effects of the linseed triple-helix polysaccharides (FHP-1) on the survival rates of HepG2.2.15 cells were shown in FIG. 8 (*a*). The survival rates were all higher than 90%, indicating that FHP-1 had no inhibiting effect on the HepG2.2.15 cells.

The activated HepG2.2.15 cells in the logarithmic growth phase were cultured in 6 cm culture plates for 24 hr, at a concentration of 500,000 cells/culture plate. The groups which were added with the linseed triple-helix polysaccharides, as the drug groups, were cultured for 24 h, with the group having no drug as a negative control, and the group which was added with 20 g/mL Lamivudine as a positive control. The culture supernatants were collected, and the fresh cell media were added to dilute the supernatants by 100 times for detecting HBsAg, and by 10 times for detecting HBeAg, and the HBV-DNA contents in the supernatants of the different concentration groups were detected. HBeAg and HBsAg were detected according to the kit's instructions, and HBV-DNA was detected according to a common QPCR kit's instructions. The absorbance of each well was measured on a microplate reader at 450 nm. The results were shown in FIG. 8 (*b*), (*c*), and (*d*), respectively. These results indicated that as compared to the blank control, the FHP-1 drug groups significantly inhibited the secretion of HBeAg and HBsAg, as well as the replication of HBV-DNA, thus showing significant effects on resisting HBV virus.

Example 7. Immunoactivity Assay of the Linseed Triple-Helix Polysaccharides (FHP-1)

Figure 9:
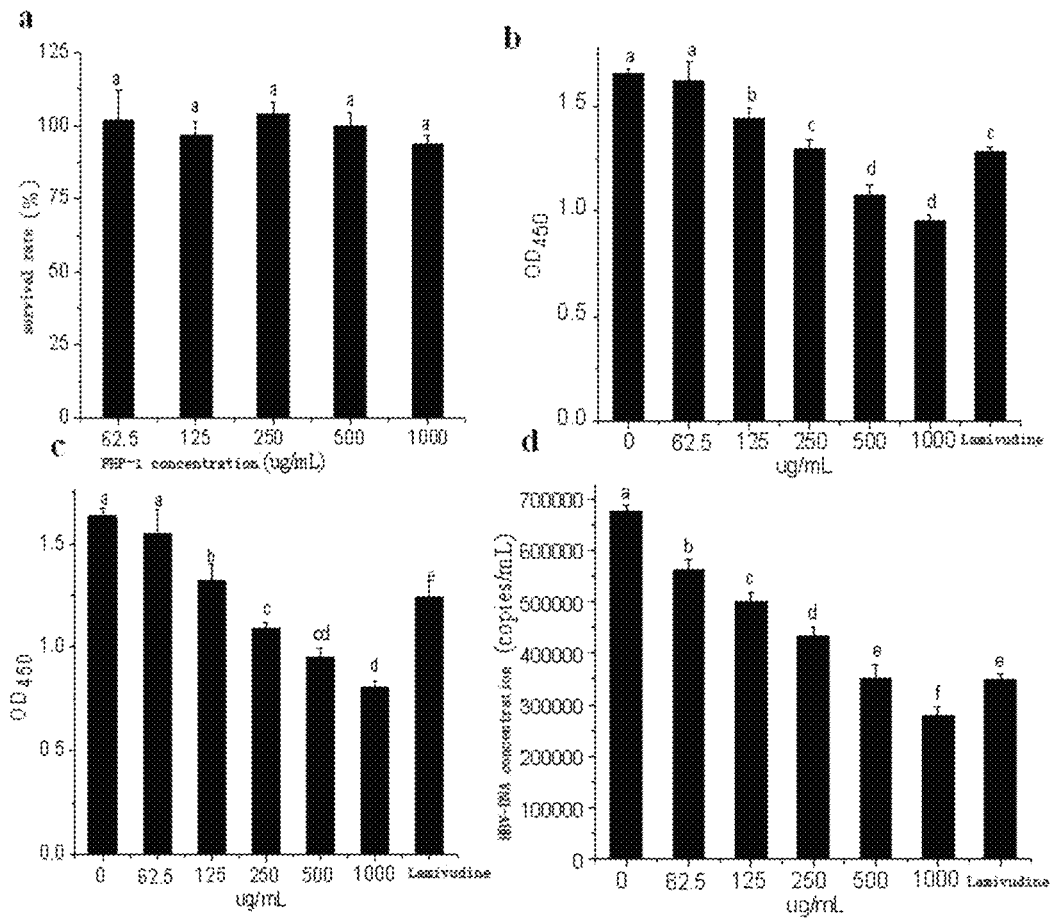
FIG. 9 shows the effects of the linseed triple-helix polysaccharide (FHP-1) on the antiviral activity of HepG2.2.15 cells, the positive control Lamivudine has a concentration of 20 μg/mL, wherein a shows the diagram of effects of the linseed triple-helix polysaccharides (FHP-1) on the survival rates of HepG2.2.15 cells; b, c, and d are diagrams respectively showing the effects of the linseed triple-helix polysaccharides (FHP-1) on HbeAg, HBsAg and DNA.
Figure 10:
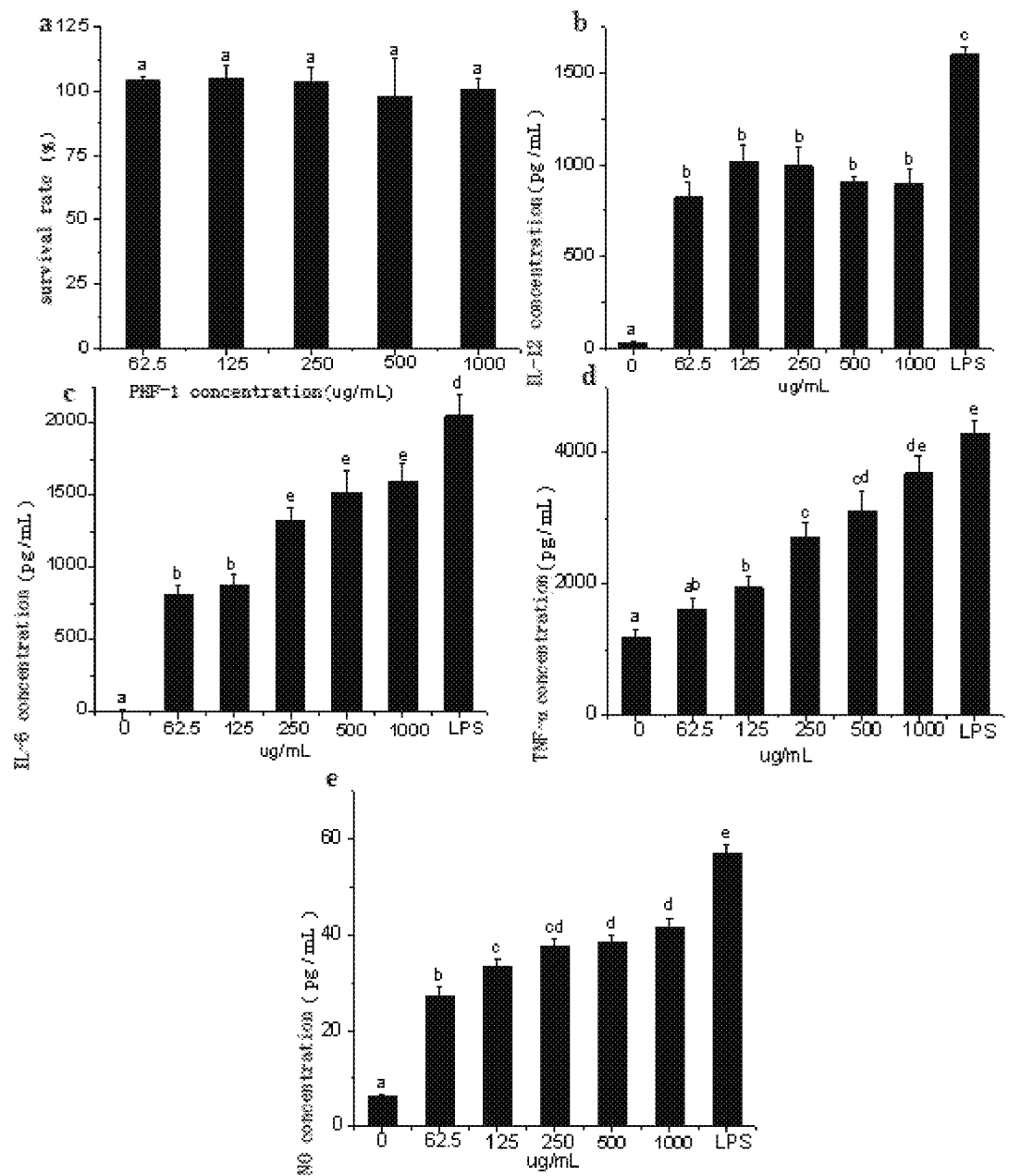
FIG. 10 shows the effects of the linseed triple-helix polysaccharides (FHP-1) on the immunity activity of the RAW 264.7 cells, and the positive control lipopolysaccharide has a concentration of 50 μg/mL, wherein a shows the effects of the linseed triple-helix polysaccharides (FHP-1) on the survival rates of the RAW 264.7 cells; b, c, d, and e are diagrams respectively showing the effects of the linseed triple-helix polysaccharides (FHP-1) on the induction of IL-12, TNF-α, IL-6, and NO.

MTT assay: RAW264.7 cells were seeded in a 96-well plate at a concentration of $1\times10^6$ cells/mL, cultured at 37° C., under 5% $CO_2$ for 24 h, then removed the supernatants and replaced fresh culture medium. The groups which were added with 20 μL linseed triple-helix polysaccharides, as the drug groups, were continued to culture for 24 h, with the group having no drugs as a blank control, and the group which was added with 20 μg/mL lipopolysaccharide as a positive control. 20 μL MTT solutions were added, continued to culture for 4 h, then stopped to culture. The culture medium in the well was aspirated. 150 μL dimethyl sulfoxide was added into each well. The plates were shaken at a low speed in a shaker for 10 min until the crystals were fully dissolved. The results were shown in FIG. 9 (a). They showed that the effects of the linseed triple-helix polysaccharides (FHP-1) on the survival rates of the RAW 264.7 cells. The survival rates were all higher than 90%, indicating that FHP-1 had no inhibiting effects on the RAW 264.7 cells.

Mouse peritoneal macrophages were added into 96-well plate and cultured for 24 h. 100 μL the samples to be detected were added and continued to culture for 36 h. The subsequent experiments were carried out according to the IL-6, IL-12, TNF-α and NO ELISA kit's instructions. The results were shown in FIG. 9 (d), (b), (c), (e) respectively. The results showed that, compared to the blank control group, the drug groups significantly increased the secretions of tumor necrosis factor TNF-α, interleukin IL-6 and IL-12, and inflammatory factor NO from the mouse macrophage Raw264.7 cells, thus showing significant antiviral activity as well as immunoregulation function.

Toxicity assay showed that the FHP-1 polysaccharides of the present invention, at a concentration of 1000 mg/mL, had no cytotoxicity on HepG2.2.15 and RAW264.7 cells. As compared to the blank control group, the FHP-1 drug groups significantly reduced the expressions of hepatitis B surface antigen (HBsAg) and the hepatitis B e-antigen (HBeAg), and inhibited the expression level of the hepatitis B virus DNA, at mean time FHP-1 significantly increased the secretions of tumor necrosis factor TNF-α, interleukin IL-6 and IL-12, and inflammatory factor NO from the mouse macrophage Raw264.7 cells, thus showing significant antiviral activity and immunoregulation function. Therefore, the FHP-1 polysaccharides of the present invention can be used in the medicaments for preventing HBV and the foods and healthcare products for improving the body's immune functions. The method for preparing the linseed polysaccharides in the present invention is simple and reliable and can be implemented on a large scale.

Example 8. Application of the Products Comprising the Linsee Triple-Helix Polysaccharides (FHP-1)

The obtained linseed triple-helix polysaccharides were added into a commercially available fruit juice in a ratio of 1‰, and observed the changes in the physical properties, such as color, turbidity, viscosity and the like.

Example 9. Application of the Products Comprising the Linseed Triple-Helix Polysaccharides (FHP-1)

The obtained linseed triple-helix polysaccharides were added into a commercially available fruit juice in a ratio of 5‰, and observed the changes in the physical properties, such as color, turbidity, viscosity and the like, thus achieving the application of the prepared linseed polysaccharides in the food products.

The above examples are the preferred embodiments of the present invention, but the embodiments of the present invention are not limited thereto, and any other changes, modifications, substitutions, combinations and simplifications, all in the equivalent replacement modes, without departing from the spirit and principle of the present invention, are all embraced in the scope of protection of the present invention.

The invention claimed is:

1. A method for preparing a linseed polysaccharide, comprising:
 (1) separation of the husks from the kernels of the linseeds: pulverizing the linseeds, sieving the pulverized linseeds to form linseed powder, then thoroughly mixing the linseed powder(s) with ethanol and glycerol, centrifuging for 20-30 minutes, and respectively collecting the linseed kernels in the upper layer and depositing the linseed husks in the bottom layer, wherein the volume ratio between the glycerol and the ethanol is 15: 3-4;
 (2) extraction of the linseed polysaccharides: extracting polysaccharides from the linseed husks obtained in step (1) by microwave-assisted hot water extraction, sieving the extracted solutions, collecting the concentrated solutions, and freeze-drying the concentrated solutions under vacuum;
 (3) separation of the linseed polysaccharides: deproteinizing the freeze-dried crude extracts obtained in step (2) by Sevage method to obtain a first supernatant, the first supernatant being subject to the Sevage method for 25-30 times to obtain a final supernatant; adding anhydrous ethanol into the final supernatants, standing for precipitation for 4-12 h, centrifuging at a speed of 3500-5000 r/min for 20-30 min to obtain precipitates, and freeze-drying the precipitates under vacuum, so as to obtain the linseed husk crude polysaccharides; wherein the Sevage method comprises mixing the freeze-dried crude extract obtained in step (2) or the first supernatant with Sevage reagent in a volume ratio of 1: 1-1:3, shaking for 20-30 min, centrifuging at a speed of 3500-5000 r/min; and wherein the Sevage reagent comprises chloroform and n-butanol with a volume ratio of 3: 1-5:1; and
 (4) purification of the linseed polysaccharides: formulating the linseed husk crude polysaccharides obtained in step (3) into 5-8 mg/mL solutions, purifying by a chromatographic column A, eluting with water, and detecting the polysaccharides by a phenol-sulfuric acid method, combining the collection liquids showing a positive result in the sugar reaction, concentrating by rotary evaporation at 50-60° C., dialyzing, then freeze-drying under vacuum; formulating the dried polysaccharides into 2-5 mg/mL solutions, purifying by a chromatographic column B, eluting with distilled water, collecting the polysaccharide components, dialyzing, ultra-filtrating, concentrating and freeze-drying, so as to obtain the linseed polysaccharide.

2. The method for preparing a linseed polysaccharide according to claim 1, wherein the linseeds are pulverized, then sieved via a 20-mesh sieve.

3. The method for preparing a linseed polysaccharide according to claim 1, wherein the microwave-assisted hot water extraction in step (2) is carried out under the conditions: solid-to-liquid ratio is 1: 20-1:30 (w/v), the extraction temperature is 60-100° C., the extraction time is 40-60 min, the output power is 600-800W, the stirring speed is 600-900 r/min, and the extracted solution obtained by the microwave-assisted hot water extraction is sieved via a 100-mesh sieve.

4. The method for preparing a linseed polysaccharide according to claim 1, wherein in step (3), the amount of the anhydrous ethanol is 3-5 times of the volume of the linseed husk crude polysaccharide solution, and after the anhydrous ethanol is added, the solution is stood for precipitation at 4° C. for 4-12 h.

5. The method for preparing a linseed polysaccharide according to claim 1, wherein in step (4), the chromatographic column A is a DEAE-Sepharose Fast Flow ion exchange column, the chromatographic column B is a Sephadex G-100 Sephadex gel column; the membrane in the ultra-filtration process has a molecular weight cutoff of $1\times10^6$ Da; the dialysis time is 48 hr, and the dialysis bag has a molecular weight cutoff of 3000-5000 Da.

* * * * *

UNITED STATES PATENT AND TRADEMARK OFFICE
CERTIFICATE OF CORRECTION

PATENT NO. : 10,835,552 B2  
APPLICATION NO. : 15/741530  
DATED : November 17, 2020  
INVENTOR(S) : Yong Wang et al.

Page 1 of 1

It is certified that error appears in the above-identified patent and that said Letters Patent is hereby corrected as shown below:

On the Title Page

Item (56), Column 2, Other Publications, Line 2, Delete "(Engeenering," and insert -- (Engineering, --

Item (57), Column 2, Abstract, Line 3, Delete "healthare" and insert -- healthcare --

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*